(12) United States Patent
Park et al.

(10) Patent No.: US 10,696,623 B2
(45) Date of Patent: Jun. 30, 2020

(54) PHENOLIC ACID DERIVATIVE COMPOUND AND USE THEREOF

(71) Applicant: DAEBONG LS, LTD, Incheon-si (KR)

(72) Inventors: Jin Oh Park, Seoul (KR); Ji Won Lee, Seoul (KR); Jae Young Lee, Gunpo-si (KR); Hye Ja Lee, Seongwipo-si (KR); Bo kyung Kwon, Gwangmyeong-si (KR)

(73) Assignee: DAEBONG LS, LTD, Incheon-si (KR)

( * ) Notice: Subject to any disclaimer, the term of this patent is extended or adjusted under 35 U.S.C. 154(b) by 0 days.

(21) Appl. No.: 16/060,734

(22) PCT Filed: Dec. 9, 2016

(86) PCT No.: PCT/KR2016/014470
§ 371 (c)(1),
(2) Date: Jun. 8, 2018

(87) PCT Pub. No.: WO2017/099531
PCT Pub. Date: Jun. 15, 2017

(65) Prior Publication Data
US 2018/0362448 A1  Dec. 20, 2018

(30) Foreign Application Priority Data

Dec. 10, 2015 (KR) .......................... 10-2015-0175779

(51) Int. Cl.
| | | |
|---|---|---|
| C07C 233/83 | (2006.01) | |
| A61K 8/46 | (2006.01) | |
| A61Q 19/02 | (2006.01) | |
| A61K 8/44 | (2006.01) | |
| A61Q 19/08 | (2006.01) | |
| C07C 235/52 | (2006.01) | |
| A61P 39/06 | (2006.01) | |
| A61P 17/00 | (2006.01) | |
| A61K 8/42 | (2006.01) | |
| C07C 327/34 | (2006.01) | |

(52) U.S. Cl.
CPC .............. *C07C 233/83* (2013.01); *A61K 8/42* (2013.01); *A61K 8/44* (2013.01); *A61K 8/46* (2013.01); *A61P 17/00* (2018.01); *A61P 39/06* (2018.01); *A61Q 19/02* (2013.01); *A61Q 19/08* (2013.01); *C07C 235/52* (2013.01); *C07C 327/34* (2013.01)

(58) Field of Classification Search
CPC ... C07C 233/83; C07C 327/34; C07C 235/52; A61K 8/42; A61K 8/44; A61K 8/46; A61P 39/06; A61P 17/00; A61P 17/04–18; A61Q 19/02
See application file for complete search history.

(56) References Cited

FOREIGN PATENT DOCUMENTS

| | | | |
|---|---|---|---|
| CN | 1439632 A | * | 9/2003 |
| KR | 10-2011-0129516 A | | 12/2011 |
| KR | 10-2012-0053245 A | | 5/2012 |
| KR | 10-2014-0084032 A | | 7/2014 |
| KR | 10-1651605 B1 | | 8/2016 |

OTHER PUBLICATIONS

Sakaguchi, N. et al., "Cell Death-inducing Activity by Gallic Acid Derivatives", Biol. Pharm. Bull., 1999, vol. 22, No. 5, pp. 471-475.
Silvia, V. et al., "Novel Molecular Combination Deriving from Natural Aminoacids and Polyphenols: Design, Synthesis and Free-radical Scavenging Activities", Eur. J. Med. Chem., 2012, vol. 50, pp. 383-392.

* cited by examiner

*Primary Examiner* — H. Sarah Park
(74) *Attorney, Agent, or Firm* — Novick, Kim & Lee, PLLC; Jae Youn Kim (57) ABSTRACT

The present invention relates to a novel phenolic acid derivative compound with whitening and antioxidant activities and use thereof. The phenolic acid derivative compound is a compound represented by Formula 1, which is described in the specification, an isomer thereof or a salt thereof. The compound of the present invention has skin whitening activity to inhibit tyrosinase, thus being suitable for use in a pharmaceutical composition or cosmetic product for skin whitening. In addition, the compound of the present invention is suitable for the prevention or treatment of oxidation-derived skin abnormality or disease such as skin aging due to its antioxidant activity.

6 Claims, 3 Drawing Sheets

PHENOLIC ACID DERIVATIVE COMPOUND AND USE THEREOF

TECHNICAL FIELD

The present invention relates to a novel phenolic acid derivative compound with whitening and antioxidant activities and use thereof.

BACKGROUND ART

Women want to have skin as white and clear as white jade and consider white and clear skin as an important standard of beauty. Thus, whitening agents for treating abnormal skin pigmentation and satisfying the desire for beauty are under active development.

Human skin color is determined by the amounts of melanin, carotene, and hemoglobin. Particularly, melanin has the greatest influence on skin color. Accordingly, control over melanogenesis is considered the most important task for the development of whitening agents.

Melanin is a phenolic polymer that takes the form of a complex of dark pigments and proteins. Melanin is produced from tyrosine through complex processes by the action of tyrosinase present in melanocytes and is a very important and essential substance that protects skin cells against UV-induced damage due to its function of blocking UV light.

Melanin is excessively produced when skin responds to external stimuli, for example, UV light, environmental pollution or stress. Excessive melanin is not released out of the skin but is transferred to keratinocytes and accumulate in the epidermis, causing severe aesthetic problems, such as stains, freckles, and senile lentigo. Excessive melanin promotes skin aging and leads to even skin cancer.

Melanogenesis is largely controlled by two methods well known in the art: a bleaching method for reducing melanin; and a method for inhibiting the activity of tyrosinase, a melanogenesis enzyme. Tocopherol and vitamins are known to be used to reduce melanin. Whitening agents using tocopherol or vitamins are known to be insignificantly effective in skin bleaching. Thus, inhibitors capable of inhibiting the activity of tyrosinase to suppress melanogenesis are attracting attention.

Substances capable of inhibiting the activity of tyrosinase, such as kojic acid and arbutin, hydroquinone, vitamin C (L-Ascorbic acid) and its derivatives, and a variety of plant extracts have been used as whitening ingredients in the cosmetic field. However, these whitening ingredients tend to be degraded and discolored owing to their poor stability in prescription systems, produce off-odors, give unclear efficacy and effectiveness at the biological level, and cause stability problems, which limit their use. Kojic acid chelates copper ions present at active sites of tyrosinase to inhibit the activity of the enzyme but causes stability problems when blended in cosmetic products. Vitamin C and its derivatives are prone to oxidation. Due to their instability, vitamin C and its derivatives are difficult to use as raw materials for cosmetic products. Hydroquinone is very effective in skin whitening but is highly irritant to skin to cause allergies, toxicity to melanocytes, and permanent skin bleaching. In recent years, hydroquinone has been listed as a carcinogen and its use has been forbidden. Only a limited concentration of hydroquinone is currently allowed in most countries around the world. Arbutin is a glucoylated hydroquinone and believed to be have the function of suppressing the synthesis of melanin without toxicity to humans, but still remains evaluation of suitability because of arbutin tends to be partially degraded by skin enzymes. Therefore, there is an urgent need to develop an alterative whitening agent that has improved efficacy even when used in a small amount and is safe without substantially causing side effects.

Breakdown of enzymatic and non-enzymatic antioxidant defense systems of the skin by reactive oxygen results in damage to cell constituents such as proteins, lipids, and DNA (Kor. J. Biotechnol. Bioeng. 2005, 20(1), 40-45). Such damage to cell constituents indicates the incidence of oxidation-associated diseases, i.e. skin aging, wrinkling, and pigmentation.

Scavenging of reactive oxygen species to prevent oxidation derived aging of cells is the most important function of antioxidant activity. The ability of a substance with antioxidant activity to scavenge reactive oxygen species can be associated with the ability of the substance to protect the skin. Melanin is synthesized in melanocytes found in the basal layer of the epidermis. Inflammation-mediating substances caused by reactive oxygen species are known to induce and stimulate melanogenesis in melanocytes. Antioxidants do not exhibit direct whitening effects but can be associated with inhibitory effects on pigmentation.

With this point of view, antioxidants capable of reacting with free radicals are used for the purpose of preventing oxidative cell damage caused by free radicals. Synthetic antioxidants, such as butylated hydroxyanisole (BHA), butylated hydroxytoluene (BHT), propyl gallate (PG), and tertiarybutyl hydroquinone (TBHQ), are mainly used in foods and pharmaceuticals. However, these antioxidants are known to cause liver hypertrophy or to be involved in carcinogenesis when administered in high doses to experimental animals. In particular, butylated hydroxytoluene is known to increase microsomal enzyme activity in the liver of experimental animals based on many experimental results andthe safety of these phenolic synthetic antioxidants is under debate, with the result that their amountsare legally regulated (Brannen A L, J. Amer. Oil Chem. Soc., 52, pp 59-63, 1975; Ito N et al., J. Natl. Cancer Inst., 70, p 343, 1983; Chan K M et al., J. Food. Sci., 58, ppl-4, 1993). Underthese circumstances, much research has been conducted with high expectations to develop safe and economical natural antioxidants of plant origin that have excellent antioxidant effects (Larson R A, Phytochemistry, 27, pp 969-978, 1988). Along with recent intensive research on natural substances, secondary metabolites present in natural sources have become major concerns as bioactive substances. Particularly, research on antioxidant substances is actively underway. Tocopherols, flavonoids, gossypols, sesamols, oryzanols, and vitamin C are currently known as natural antioxidants (Huson B et al., Food Chem., 19, pp 537-541, 1987; Frankel, E. N. Food Chem., 57, p 51, 1996; Giese J, Food Technol., 5, pp 73-81, 1996; Pszcczola D E, Food Tech., 55, pp 51-59, 2001). Tocopherol and L-ascorbic acid are used as natural antioxidants in preference to others. Tocopherol is highly safe but its ability to prevent oxidation is poor when used alone and its price is high (Halliwell B et al., FASEB J., 2, pp 2867-2870, 1988).

Thus, there is a need to develop an alternative antioxidant substance that can prevent conditions and diseases, including aging, caused by oxidative damage.

DETAILED DESCRIPTION OF THE INVENTION

Problems to be Solved by the Invention

The present invention has been made in an effort to solve the problems of the prior art and it is one object of the present invention to provide a novel compound with skin whitening activity.

It is another object of the present invention to provide a novel compound with antioxidant activity.

Means for Solving the Problems

One aspect of the present invention provides a compound represented by Formula 1:

[Formula 1]

wherein n is 0 or 1, X is NH or S, Y is $C_1$-$C_2$ alkyl, $R_1$ is $C_1$-$C_8$hydroxyalkyl, $C_1$-$C_8$hydroxyaryl, $C_1$-$C_8$hydroxyalkylaryl, an amino group or an amide group, $R_2$ is H or $C_1$-$C_3$ alkyl, and each $R_3$ is H or methyl, an isomer thereof or a salt thereof.

A further aspect of the present invention provides a compound represented by Formula 2:

[Formula 2]

wherein $R_2$ is H or $C_1$-$C_3$ alkyl, each $R_3$ is H or methyl, and $R_4$ is benzyl, hydroxymethyl or hydroxyethyl, an isomer thereof or a salt thereof.

Another aspect of the present invention provides a compound represented by Formula 3:

[Formula 3]

wherein $R_2$ is H or $C_1$-$C_3$ alkyl, each $R_3$ is H or methyl, and $R_5$ is an amino group or a $C_1$-$C_3$ amide group, an isomer thereof or a salt thereof.

Another aspect of the present invention provides (S)-ethyl-3-phenyl-2-(3,4,5-trihydroxybenzamido)propanoate, (R)-ethyl-2-amino-3-(4-hydroxy-3,5-dimethoxybenzoyl-thio)propanoate, (R)-methyl-2-acetoamido-3-(4-hydroxy-3,5-dimethoxybenzoylthio)propanoate, (S)-methyl-3-hydroxy-2-(4-hydroxy-3,5-dimethoxybenzoylthio)propanoate, (2S,3R)-methyl-3-hydroxy-2-(4-hydroxy-3,5-dimethoxybenzoylthio)butanoate, an isomer thereof or a salt thereof.

Another aspect of the present invention provides a composition for skin whitening including any of the compounds described herein, isomer thereof or salt thereof as an active ingredient.

Another aspect of the present invention provides an antioxidant composition for preventing or treating an oxidation derived skin abnormality or disease including any of the compounds described herein, isomer thereof or salt thereof as an active ingredient.

The oxidation derived skin abnormality or disease is selected from skin aging, wrinkling, skin pigmentation, and combinations thereof.

Yet another aspect of the present invention provides a cosmetic composition including 0.01 to 10% by weight of any of the compounds described herein, isomer thereof or salt thereof.

Effects of the Invention

The compounds of the present invention have skin whitening activities by inhibition of tyrosinase and melanogenesis, thus being suitable for use in pharmaceutical compositions and cosmetic ingredients for skin whitening. In addition, the compounds of the present invention are suitable for the prevention or treatment of oxidation derived skin abnormality or diseases such as skin aging due to their antioxidant activities.

BEST MODE FOR CARRYING OUT THE INVENTION

The present invention will now be explained in detail.
The present invention provides a compound represented by Formula 1:

[Formula 1]

wherein n is 0 or 1, X is NH or S, Y is $C_1$-$C_2$ alkyl, $R_1$ is $C_1$-$C_8$hydroxyalkyl, $C_1$-$C_8$hydroxyaryl, $C_1$-$C_8$hydroxyalkylaryl, an amino group or an amide group, $R_2$ is H or $C_1$-$C_3$ alkyl, and each $R_3$ is H or methyl, an isomer thereof or a salt thereof.

The compound of Formula 1 is a derivative compound that has a main skeleton of gallic acid or syringic acid as a naturally occurring phenolic acid and is prepared by reaction of the naturally occurring phenolic acid with an amino acid. The compound of Formula 1 was designed and synthesized using the natural substances whose toxicities are well known. Accordingly, the pharmacological and toxicological mechanisms of metabolites or degradation products of the phenolic acid derivative compound are well known, ensuring safety of the derivative compounds when used.

In view of this, the amino acid is preferably selected from amino acids that are metabolized or used in the human body and essential amino acids. Examples of such amino acids include alanine, cysteine, aspartic acid, glutamic acid, phenylalanine, glycine, histidine, isoleucine, lysine, leucine, methionine, asparagine, proline, glutamine, arginine, serine, threonine, selenocysteine, valine, tryptophan, and tyrosine. The amino acid is preferably cysteine (including one substituted with an acetyl group), phenylalanine, serine or threonine in terms of ease of synthesis and efficacy/effectiveness.

The compound of Formula 1 can be synthesized as depicted in the following reaction scheme.

In the reaction scheme, step 1) is the protection of the hydroxyl group with an acetyl group for the subsequent reaction, step 2) is the activation of the carboxylic acid group of the benzoic acid moiety followed by coupling reaction with an amino acid to synthesize the corresponding amide compound, and step 3) is the deprotection of the acetyl group into a hydroxyl group to synthesize the desired phenolic derivative compounds.

An amino acid residue generally refers to a moiety without $H_2O$ formed by the hydrogen of the amino group and the OH of the carboxyl group. In contrast, the term "amino acid residue" as used herein refers to an amino acid-derived residual structure that remains after reaction of the reactive functional group of the amino acid with gallic acid or syringic acid. The structure of the amino acid residue may vary depending on the type of the amino acid. The amino acid residue may include a reactive functional group of the amino acid that remain without further reaction. That is, the structure of the amino acid residue is determined by the type of the amino acid and the combination of the amino acid and gallic acid or syringic acid. Particularly, the amino acid residue may include a sulfur or amine moiety depending on the nucleophilic site of the amino acid where the reaction takes place.

Specifically, the compound represented by Formula 1, isomer thereof or salt thereof may be a compound represented by Formula 2:

[Formula 2]

wherein $R_2$ is H or $C_1$-$C_3$ alkyl, each $R_3$ is H or methyl, and $R_4$ is benzyl, hydroxymethyl or hydroxyethyl, an isomer thereof or a salt thereof.

Alternatively, the compound represented by Formula 1, isomer thereof or salt thereof may be a compound represented by Formula 3:

[Formula 3]

wherein $R_2$ is H or $C_1$-$C_3$ alkyl, each $R_3$ is H or methyl, and $R_5$ is an amino group or a $C_1$-$C_3$ amide group, an isomer thereof or a salt thereof.

More specifically, the compound represented by Formula 2 or 3, isomer thereof or salt thereof may be(S)-ethyl-3-phenyl-2-(3,4,5-trihydroxybenzamido)propanoate, (R)-ethyl-2-amino-3-(4-hydroxy-3,5-dimethoxybenzoylthio) propanoate, (R)-methyl-2-acetoamido-3-(4-hydroxy-3,5-dimethoxybenzoylthio)propanoate, (S)-methyl-3-hydroxy-2-(4-hydroxy-3,5-dimethoxybenzoylthio)propanoate or (2S, 3R)-methyl-3-hydroxy-2-(4-hydroxy-3,5-dimethoxybenzoylthio)butanoate.

The compound, isomer thereof or salt thereof according to the present invention can be used for skin whitening due to its ability to inhibit melanogenesis and tyrosinase. The compound, isomer thereof or salt thereof according to the present invention can also be used to prevent or treat an oxidation-derived skin abnormality or disease due to its superior antioxidant effect. The oxidation-derived skin abnormality or disease may be skin aging, wrinkling, skin pigmentation, inflammatory disease, senile degenerative disease, psoriasis or eczema, particularly skin aging, wrinkling or skin pigmentation.

Preferably, the compound, isomer thereof or salt thereof according to the present invention is used to prepare a cosmetic composition. The compound, isomer thereof or salt thereof according to the present invention may also be used to prepare a pharmaceutical composition or a health functional food. However, there is no restriction on the use of the compound, isomer thereof or salt thereof.

The cosmetic composition may be prepared into any suitable formulation known in the art. Examples of such formulations include, but are not limited to, solutions, suspensions, emulsions, pastes, gels, creams, lotions, powders, oils, powder foundations, emulsion foundations, wax foundations, and sprays. More specifically, the cosmetic composition may be prepared into a sun cream, an emollient lotion, an astringent lotion, a nutrient lotion, a nutrient cream, a massage cream, an essence, an eye cream, a pack, a spray or a powder. The cosmetic composition may include 0.01 to 10% by weight of the compound, isomer thereof or salt thereof. If the compound, isomer thereof or salt thereof is present in an amount less than 0.01% by weight with respect to the weight of the composition, the desired effect may be insignificant. Meanwhile, if the compound, isomer thereof or salt thereof is present in an amount exceeding 10% by weight with respect to the weight of the composition, the formulation stability and storage stability of the composition may be poor.

The pharmaceutical composition may be prepared into an oral formulation, such as a powder, a granule, a tablet, a capsule, a suspension, an emulsion, a syrup or an aerosol, an external formulation, a suppository, or a sterile injectable solution according to conventional methods. The pharmaceutical composition may further include an appropriate carrier, excipient or diluent known in the art. Examples of carriers, excipients or diluents suitable for use in the pharmaceutical composition include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oils.

The health functional food may be provided in the form of a powder, granule, tablet, capsule, syrup or beverage. The health food may be used in combination with other foods or food additives in addition to the compound of the present invention as the active ingredient. These foods or food additives may be appropriately used according to general methods known in the art. The amount of the active ingredient used may be appropriately determined according to its purpose of use, for example, prophylactic, health or therapeutic treatment.

The kind of the health food is not particularly limited and examples thereof include meats, sausages, breads, chocolates, candies, snacks, cookies, pizza, instant noodles, other noodles, gums, dairy products (including ice creams), soups, beverages, teas, drinks, alcoholic drinks, and vitamin complexes.

The present invention will be explained in more detail with reference to the following examples. These examples are merely illustrative and are not intended to limit the scope of the invention.

EXAMPLES

Example 1

Preparation of (S)-ethyl-3-phenyl-2-(3,4,5-trihydroxybenzamido)propanoate (1) Preparation of (S)-ethyl-3-phenyl-2-(3,4,5-triacetoxybenzamido)propanoate In a 100 mL flask, 3,4,5-triacetoxybenzoic acid (3.55 g), dichloromethane (12 mL) and DMF (0.1 mL) were added and was stirred at 5° C. To the mixture was added dropwise oxalyl chloride (1.7 mL). After stirring the resulting mixture for 6 h at room temperature, the reaction solution was concentrated fully under reduced pressure to afford 3,4,5-triacetoxybenzoyl chloride.

(S)-phenylalanine ethyl ester hydrochloride (2.75 g), dichloromethane (12 mL), and diisopropylethylamine (6.2 mL) were stirred in a 100 mL flask at 5° C. and a solution of the 3,4,5-triacetoxybenzoyl chloride in dichloromethane (10 mL) was added dropwise. After stirring the mixture for 3 h at room temperature, the reaction mixture was concentrated at reduced pressure. The resulting solid was dissolved in ethyl acetate (50 mL) and washed with water, a saturated aqueous solution of sodium bicarbonate, and saturated brine. The organic layer was dried over anhydrous magnesium sulfate and filtered. The filtrate was concentrated under reduced pressure and purified by column chromatography to give 4.43 g (yield 78%) of the desired product as a white solid.

(2) Preparation of (S)-ethyl-3-phenyl-2-(3,4,5-trihydroxybenzamido)propanoate The (S)-ethyl-3-phenyl-2-(3,4,5-triacetoxybenzamido)propanoate (2.83 g) prepared in (1) was dissolved in ethanol (6 mL) and a 4M solution of hydrochloric acid (in 1,4-dioxane, 10 mL) was added thereto. The mixture was stirred at room temperature for 8 h, concentrated under reduced pressure, and purified by column chromatography to give 1.9 g (yield 92%) of the desired product.

$^1$H NMR (400 MHz, CDCl$_3$) δ 1.35 (t, J=6.8 Hz, 3H), 3.10-3.17 (m, 2H), 4.07-4.13 (m, 2H), 4.90-4.95 (m, 2H), 6.83 (s, 2H), 7.01-7.20 (m, 5H), 7.14 (d, J=7.2 Hz, 1H), 7.65-7.25 (br, 3H); [α]$^{20.0}_D$=−42.97 (c=1, CH$_3$OH); FT-IR (Neat) 3358.43 cm$^{-1}$, 2983.34 cm$^{-1}$, 1728.87 cm$^{-1}$, 1601.59 cm$^{-1}$, 1514.81 cm$^{-1}$, 1444.42 cm$^{-1}$, 1324.86 cm$^{-1}$, 1274.72 cm$^{-1}$, 1203.36 cm$^{-1}$, 1092.48 cm$^{-1}$, 1034.62 cm$^{-1}$, 862.99 cm$^{-1}$, 748.25 cm$^{-1}$, 701.96 cm$^{-1}$; MS(ESI): m/z=346.1 [M+H]$^+$

Example 2

Preparation of (R)-ethyl-2-amino-3-(4-hydroxy-3,5-dimethoxybenzoylthio)propanoate

(1) Preparation of (R)-ethyl-2-amino-3-(4-acetoxy-3,5-dimethoxybenzoylthio)propanoate In a 100 mL flask, 4-acetoxy-3,5-dimethoxybenzoic acid (4.8 g), dichloromethane (20 mL) and DMF (0.1 mL) were added and the mixture was stirred at 5° C. To the mixture was added dropwise oxalyl chloride (2.4 mL). After stirring the resulting mixture for 6 h at room temperature, the reaction solution was concentrated fully under reduced pressure to afford 3,4,5-triacetoxybenzoyl chloride.

(R)—N-acetylcysteine ethyl ester (3.6 g), dichloromethane (20 mL), and diisopropylethylamine (10 mL) were stirred in a 100 mL flask at 5° C. and a solution of the 4-acetoxy-3,5-dimethoxybenzoyl chloride in dichloromethane (20 mL) was added dropwise thereto. After stirring the mixture for 3 h at room temperature, the reaction solution was concentrated at reduced pressure. The resulting solid was dissolved in ethyl acetate (150 mL) and washed with water, a saturated aqueous solution of sodium bicarbonate, and saturated brine. The organic layer was dried over anhydrous magnesium sulfate and filtered. The filtrate was concentrated under reduced pressure and purified by column chromatography to give 6.8 g (yield 87%) of the desired product as a white solid.

(2) Preparation of (R)-ethyl-2-amino-3-(4-hydroxy-3,5-dimethoxybenzoylthio)propanoate The (R)-ethyl-2-amino-3-(4-acetoxy-3,5-dimethoxybenzoylthio)propanoate (3.0 g) prepared in (1) was dissolved in ethanol (7 mL) and hydrazine hydrate (0.8 mL) was added thereto. After stirring the mixture for 4 h at room temperature, the reaction mixture was concentrated under reduced pressure. The resulting solid was dissolved in ethyl acetate (50 mL) and washed with water, a saturated aqueous solution of sodium bicarbonate, and saturated brine. The organic layer was dried over anhydrous magnesium sulfate and filtered. The filtrate was concentrated under reduced pressure and purified by column chromatography to give 2.0 g (yield 83%) of the desired product.

$^1$H NMR (400 MHz, CDCl$_3$) δ 1.35 (t, J=6.8 Hz, 3H), 3.09-3.22 (m, 2H), 3.96 (s, 6H), 4.25-4.37 (m, 2H), 5.03-5.05 (m, 1H), 5.86 (s, 1H), 6.95 (d, J=6.4 Hz, 1H), 7.09 (s, 2H); $[α]^{22.3}_D$=−4.80 (c=1, CH$_3$OH); FT-IR(KBr) 3364.21 cm$^{-1}$, 3302.5 cm$^{-1}$, 2996.84 cm$^{-1}$, 2977.55 cm$^{-1}$, 2963.09 cm$^{-1}$, 2931.27 cm$^{-1}$, 2834.85 cm$^{-1}$, 2570.65 cm$^{-1}$, 1724.05 cm$^{-1}$, 1648.84 cm$^{-1}$, 1609.31 cm$^{-1}$, 1509.03 cm$^{-1}$, 1458.89 cm$^{-1}$, 1421.28 cm$^{-1}$, 1368.25 cm$^{-1}$, 1347.03 cm$^{-1}$, 1322.93 cm$^{-1}$, 1304.61 cm$^{-1}$, 1284.36 cm$^{-1}$, 1245.79 cm$^{-1}$, 1224.58 cm$^{-1}$, 1213.97 cm$^{-1}$, 1193.72 cm$^{-1}$, 1120.44 cm$^{-1}$, 764.64 cm$^{-1}$, 752.10 cm$^{-1}$, 720.28 cm$^{-1}$; MS(ESI): m/z=329.9 [M+H]$^+$

Example 3

Preparation of (R)-methyl-2-acetoamido-3-(4-hydroxy-3,5-dimethoxybenzoylthio)propanoate

(1) Preparation of (R)-methyl-2-acetoamido-3-(4-acetoxy-3,5-dimethoxybenzoylthio)propanoate In a 100 mL flask, 4-Acetoxy-3,5-dimethoxybenzoic acid (3.6 g), dichloromethane (15 mL) and DMF (0.1 mL) were added and the mixture was stirred at 5° C. To the mixture was added dropwise oxalyl chloride (1.6 mL). After stirring the resulting mixture for 6 h at room temperature, the reaction solution was concentrated fully under reduced pressure to afford 4-acetoxy-3,5-dimethoxybenzoyl chloride.

(R)—N-acetylcysteine methyl ester (2.7 g), dichloromethane (15 mL), and diisopropylethylamine (4 mL) were stirred in a 100 mL flask at 5° C. and a solution of the 4-acetoxy-3,5-dimethoxybenzoyl chloride in dichloromethane (15 mL) was added dropwise thereto. After stirring the mixture for 3 h at room temperature, the reaction solution was concentrated at reduced pressure. The resulting solid was dissolved in ethyl acetate (100 mL) and washed with water, a saturated aqueous solution of sodium bicarbonate, and saturated brine. The organic layer was dried over anhydrous magnesium sulfate and filtered. The filtrate was concentrated under reduced pressure and purified by column chromatography to give 4.4 g (yield 73%) of the desired product as a white solid.

(2) Preparation of (R)-methyl-2-acetoamido-3-(4-hydroxy-3,5-dimethoxybenzoylthio)propanoate

The (R)-methyl-2-amino-3-(4-acetoxy-3,5-dimethoxybenzoylthio)propanoate (2.4 g) prepared in (1) was dissolved in methanol (10 mL) and hydrazine hydrate (0.7 mL) was added thereto. After stirring the mixture for 8 h at room temperature, the reaction mixture was concentrated under reduced pressure. The resulting solid was washed with water and hexane and purified to give 1.4 g (yield 74%) of the desired product.

$^1$H NMR (400 MHz, DMSO-d6) δ 1.84 (s, 3H), 3.21 (dd, J=8.4, 13.6 Hz, 1H), 3.48 (dd, J=4.8, 13.6 Hz, 1H), 3.64 (s, 3H), 3.81 (s, 6H), 4.43-4.48 (m, 1H), 7.15 (s, 2H), 8.47 (d, J=8.0 Hz, 1H), 9.57 (s, 1H); $[α]^{20.2}_D$=−4.39 (c=1, CH$_3$OH); FT-IR(KBr) 3497.27 cm$^{-1}$, 3285.14 cm$^{-1}$, 3068.19 cm$^{-1}$, 2958.27 cm$^{-1}$, 2934.16 cm$^{-1}$, 2837.74 cm$^{-1}$, 1749.12 cm$^{-1}$, 1641.13 cm$^{-1}$, 1614.13 cm$^{-1}$, 1541.81 cm$^{-1}$, 1511.92 cm$^{-1}$, 1457.92 cm$^{-1}$, 1421.28 cm$^{-1}$, 1402.0 cm$^{-1}$, 1378.85 cm$^{-1}$, 1326.79 cm$^{-1}$, 1311.36 cm$^{-1}$, 1282.43 cm$^{-1}$, 1255.43 cm$^{-1}$, 1223.61 cm$^{-1}$, 1189.86 cm$^{-1}$, 1143.58 cm$^{-1}$, 1106.94 cm$^{-1}$, 998.95 cm$^{-1}$, 851.42 cm$^{-1}$, 834.06 cm$^{-1}$, 772.35 cm$^{-1}$, 690.39 cm$^{-1}$; MS(ESI): m/z=357.8 [M+H]$^+$

Example 4

Preparation of (S)-methyl-3-hydroxy-2-(4-hydroxy-3,5-dimethoxybenzoylthio)propanoate (1) Preparation of (S)-methyl-3-hydroxy-2-(4-acetoxy-3,5-dimethoxybenzoylthio)propanoate In a 100 mL flask, 4-Acetoxy-3,5-dimethoxybenzoic acid (2.4 g), dichloromethane (10 mL) and DMF (0.1 mL) were added and the mixture was stirred at 5° C. To the mixture was added dropwise oxalyl chloride (1.2 mL). After stirring the resulting mixture for 6 h at room temperature, the reaction solution was concentrated under reduced pressure to afford 4-acetoxy-3,5-dimethoxybenzoyl chloride.

(S)-serine methyl ester (1.55 g), dichloromethane (15 mL), and triethylamine (2.8 mL) were stirred in a 100 mL flask at 5° C. and a solution of the 4-acetoxy-3,5-dimethoxybenzoyl chloride in dichloromethane (10 mL) was added dropwise thereto. After stirring the mixture for 3 h at room temperature, the reaction solution was concentrated at reduced pressure. The resulting solid was dissolved in ethyl acetate (100 mL) and washed with water, a 1 M aqueous solution of hydrochloric acid, a saturated aqueous solution of sodium bicarbonate, and saturated brine. The organic layer was dried over anhydrous magnesium sulfate and filtered. The filtrate was concentrated under reduced pressure and purified by column chromatography to give 2.5 g (yield 73%) of the desired product as a white solid.

(2) Preparation of (S)-methyl-3-hydroxy-2-(4-hydroxy-3,5-dimethoxybenzoylthio)propanoate The (S)-methyl-3-hydroxy-2-(4-acetoxy-3,5-dimethoxybenzoylthio)propanoate (1.4 g) prepared in (1) was dissolved in methanol (8 mL) and hydrazine hydrate (0.4 mL) was added thereto. After stirring the mixture for 4 h at room temperature, the reaction mixture was concentrated under reduced pressure. The resulting solid was washed with water and hexane to give 0.85 g (yield 69%) of the desired product.

$^1$H NMR (400 MHz, DMSO-d6) δ 3.65 (s, 3H), 3.77-3.82 (m, 8H), 4.50-4.54 (m, 1H), 5.07 (t, J=6.0 Hz, 1H), 7.22 (s, 2H), 8.44 (d, J=6.8 Hz, 1H), 8.99 (s, 1H); $[α]^{20.2}_D$=−4.39 (c=1, CH$_3$OH); FT-IR(KBr) 3472.20 cm$^{-1}$, 3281.29 cm$^{-1}$, 3172.33 cm$^{-1}$, 3034.44 cm$^{-1}$, 3017.09 cm$^{-1}$, 3001.66 cm$^{-1}$, 2975.62 cm$^{-1}$, 2948.63 cm$^{-1}$, 2907.16 cm$^{-1}$, 2844.49 cm$^{-1}$, 1749.12 cm$^{-1}$, 1634.38 cm$^{-1}$, 1606.41 cm$^{-1}$, 1536.99 cm$^{-1}$, 1509.99 cm$^{-1}$, 1470.46 cm$^{-1}$, 1451.17 cm$^{-1}$, 1424.17 cm$^{-1}$, 1375.0 cm$^{-1}$, 1348.0 cm$^{-1}$, 1314.25 cm$^{-1}$, 1294.0 cm$^{-1}$, 1241.93 cm$^{-1}$, 1227.47 cm$^{-1}$, 1187.94 cm$^{-1}$, 1141.65 cm$^{-1}$, 1120.44 cm$^{-1}$, 1059.69 cm$^{-1}$, 1027.87 cm$^{-1}$, 972.91 cm$^{-1}$, 849.49 cm$^{-1}$, 777.17 cm$^{-1}$; MS(ESI): m/z=299.9 [M+H]$^+$

Example 5

Preparation of (2S,3R)-methyl-3-hydroxy-2-(4-hydroxy-3,5-dimethoxybenzoylthio)butanoate (1) Preparation of (2S,3R)-methyl-3-hydroxy-2-(4-acetoxy-3,5-dimethoxybenzoylthio)butanoate In a 100 mL flask 4-Acetoxy-3,5-dimethoxybenzoic acid (2.64 g dichloromethane (11 mL) and DMF (0.1 mL) were added and the mixture was stirred at 5° C. To the mixture was added dropwise oxalyl chloride (1.2 mL). After stirring the resulting mixture for 6 h at room temperature, the reaction solution was concentrated under reduced pressure to afford 4-acetoxy-3,5-dimethoxybenzoyl chloride.

(S)-threonine methyl ester (1.87 g), dichloromethane (10 mL), tetrahydrofuran (10 mL), and triethylamine (3.2 mL) were stirred in a 100 mL flask at 5° C. and a solution of the 4-acetoxy-3,5-dimethoxybenzoyl chloridein dichloromethane (11 mL) was added dropwise thereto. After stirring the mixture for 3 h at room temperature, the reaction solution was concentrated at reduced pressure. The resulting solid was dissolved in ethyl acetate (100 mL) and washed with water, a 1 M aqueous solution of hydrochloric acid, a saturated aqueous solution of sodium bicarbonate, and saturated brine. The organic layer was dried over anhydrous magnesium sulfate and filtered. The filtrate was concentrated under reduced pressure and purified by column chromatography to give 2.45 g (yield 66%) of the desired product as a white solid.

(2) Preparation of (2S,3R)-methyl-3-hydroxy-2-(4-hydroxy-3,5-dimethoxybenzoylthio)butanoate The (2S,3R)-methyl-3-hydroxy-2-(4-acetoxy-3,5-dimethoxybenzoylthio)butanoate (2.1 g) prepared in (1) was dissolved in methanol (10 mL) and hydrazine hydrate (0.6 mL) was added thereto. After stirring the mixture for 3 h at room temperature, the reaction mixture was concentrated under reduced pressure. The resulting solid was dissolved in ethyl acetate (50 mL) and washed with water, a saturated aqueous solution of sodium bicarbonate, and saturated brine. The organic layer was dried over anhydrous magnesium sulfate and filtered. The filtrate was concentrated under reduced pressure and purified by column chromatography to give 1.4 g (yield 76%) of the desired product.

$^1$HNMR (400 MHz, CDCl$_3$) δ 1.30 (d, J=6.4 Hz, 3H), 2.50-3.00 (br, 1H), 3.80 (s, 3H), 3.91 (s, 6H), 4.44-4.46 (m, 1H), 4.82 (d, J=9.2, 1H), 5.98-6.03 (br, 1H), 7.01 (d, J=9.2 Hz, 1H), 7.11 (s, 2H); $[α]^{21.2}_D$=−4.45 (c=1, CH$_3$OH); FT-IR (Neat) 3366.14 cm$^{-1}$, 2975.62 cm$^{-1}$, 2844.49 cm$^{-1}$, 1742.37 cm$^{-1}$, 1640.16 cm$^{-1}$, 1604.48 cm$^{-1}$, 1542.7 cm$^{-1}$7, 1508.06 cm$^{-1}$, 1459.85 cm$^{-1}$, 1423.21 cm$^{-1}$, 1339.32 cm$^{-1}$, 1214.93 cm$^{-1}$, 1158.04 cm$^{-1}$, 1116.58 cm$^{-1}$, 1014.37 cm$^{-1}$, 912.17 cm$^{-1}$, 863.95 cm$^{-1}$, 758.85 cm$^{-1}$, 696.18 cm$^{-1}$; MS(ESI): m/z=313.9 [M+H]$^+$

[Test Example 1]—Antioxidant Effects of the Phenolic Acid Derivative Compounds

The 1,1-diphenyl-2-picrylhydrazyl (DPPH) radical scavenging activities of the phenolic acid derivative compounds prepared in Examples 1-5 were measured to evaluate the antioxidant activities of the compounds against free radicals. Ascorbic acid was used as a positive control.

1,1-Diphenyl-2-picrylhydrazyl (DPPH) radical was purchased from Sigma Chemical Co. (USA) and L-ascorbic acid purchased from Sigma (USA) were used for testing.

100 µl of a 0.2 mM DPPH solution in methanol and 100 µl of each of the compounds at different concentrations were prepared in a 96-well plate. After the reaction was allowed to proceed at room temperature for 10 min, the absorbance of each sample was measured at 517 nm.

Figure 1:
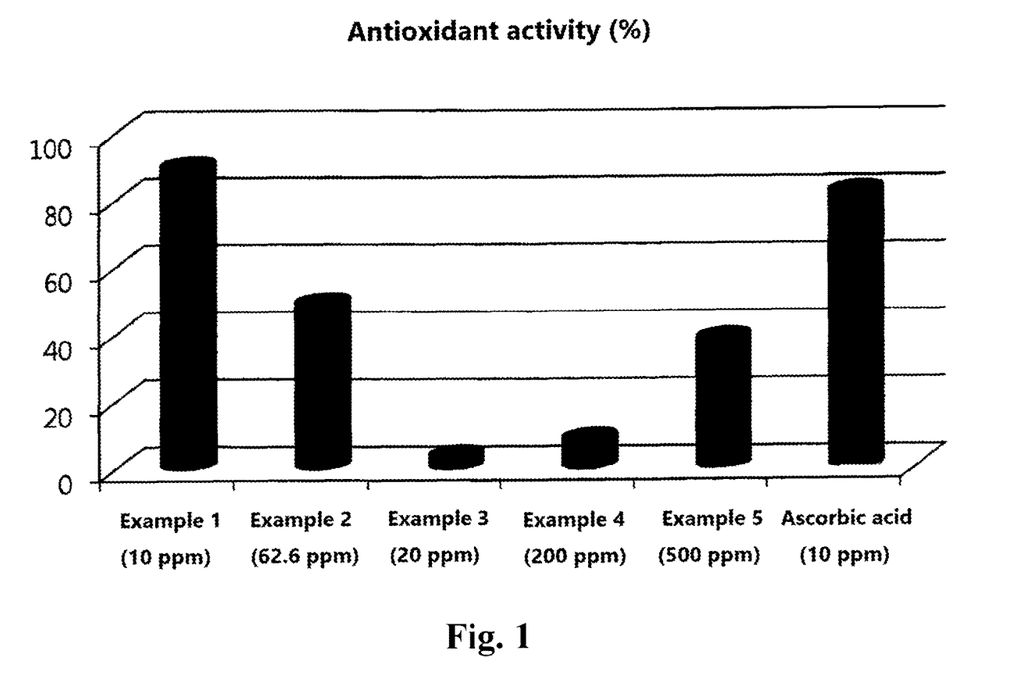
FIG. 1 shows antioxidant effects of compounds prepared in Examples 1-5.

The correlations between the absorbance and the concentration of the compounds are shown in FIG. 1.

As can be seen in FIG. 1, most of the compounds showed low activities compared to ascorbic acid but the compound of Example 1 showed a high activity compared to the control ascorbic acid.

These results can lead to the conclusion that the phenolic acid derivative compounds of Examples 1-5 can be used to prevent or treat oxidation-related diseases, including skin aging, wrinkling, and skin pigmentation, due to their potent antioxidant activities.

[Test Example 2]—Inhibitory Effects of the Phenolic Acid Derivative Compounds on Intracellular Tyrosinase Activity The inhibitory effects of the phenolic acid derivative compounds prepared in Examples 1-5 on intracellular tyrosinase activity were evaluated.

Fetal bovine serum (FBS) and Dulbecco's modified Eagle medium (DMEM) purchased from Gibco (USA) and mouse-derived B16F10 (melanoma cell line) purchased from the Korean Cell Line Bank were used for cellular experiments. Cells were cultured in DMEM (Gibco) supplemented with 10% FBS (Gibco) and 1% antibiotic-antimycotic (Gibco) in an incubator at 37° C. and 5% CO$_2$. Cells were passaged every 3-4 days. Cultured B16F10 cells were detached with 0.05% trypsin-EDTA and inoculated into each well of a 24-well plate at the same density (1.0×10$^5$ cells/well). 16 h after inoculation, the medium was replaced with a serum-free medium. Culture was continued for 6 h. Cells were treated with α-MSH (100 nM) and each test drug. Cells were cultured for additional 3 days. After completion of the culture, cells were washed twice with cold phosphate-buffered saline (PBS) and were disrupted by treatment with 200 µl of RIPA buffer supplied with protease inhibitor (50 nM Tris-HCl, 150 nM NaCl, 2% NP-40, 0.5% sodium deoxycholate, 0.1% SDS, pH7.4). The collected lysate was centrifuged (13,000 rpm) at 4° C. for 30 min. The supernatant containing the protein was collected. The protein was quantified by Bradford assay. 198 µl of the protein at a concentration of 200 µg/ml was allowed to react with 2 µl of L-DOPA at a concentration of 2 mg/ml in a CO$_2$ incubator protected from light with a cooking foil at 37° C. for 1 h. Thereafter, the absorbance was measured at 405 nm.

The intracellular tyrosinase activity was calculated as follows:

Intracellular tyrosinase activity (%)=sample group/control(treatment with factor involved in melanin biosynthesis)*100

Arbutin was used as the control. The results are shown in FIG. 2.

Figure 2:
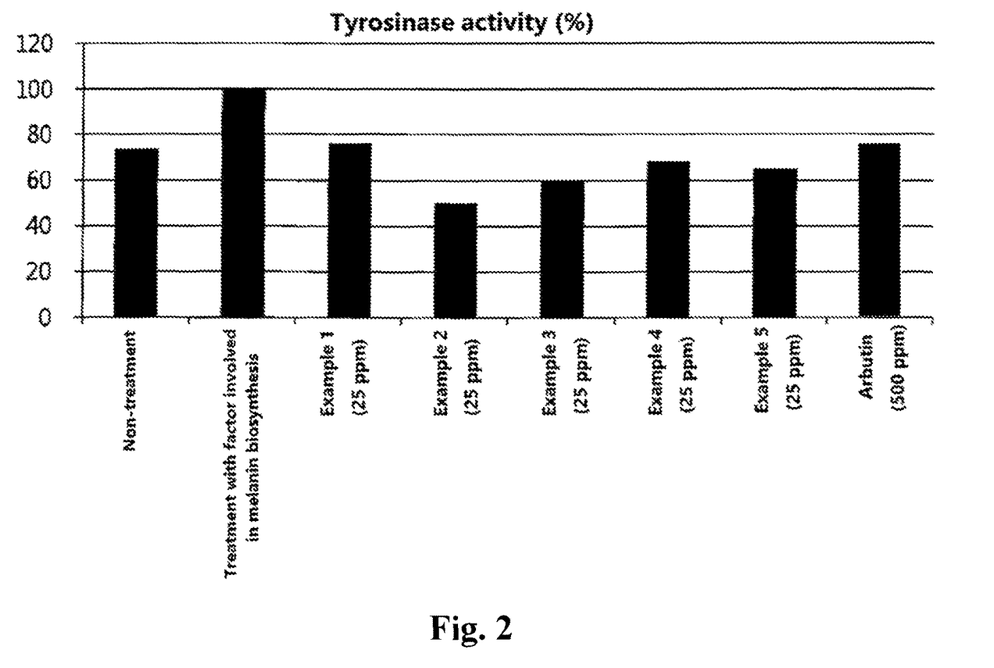
FIG. 2 shows inhibitory effects of compounds prepared in Examples 1-5 on tyrosinase activity.

As can be seen from FIG. 2, the compounds of Examples 1-5 showed better inhibitory effects on tyrosinase activity than arbutin. Thus, the amounts of intracellularly produced melanin were measured to investigate the influence of the phenolic acid derivative compounds on tyrosinase activity inhibition and melanogenesis.

[Test Example 3]—Inhibitory Effects of the Phenolic Acid Derivative Compounds on Melanogenesis The inhibitory effects of the compounds synthesized in Examples 1-5 on melanogenesis in cells were evaluated by Chang and Chen's method (Chang and Chen, 'Inhibitory effect of homochlorcyclizine on melanogenesis in α-melanocyte stimulating hormone-stimulated mouse B16 melanoma cells¦, Archives of Pharmacal Research January 2012, Volume 35, Issue 1, pp 119-127).

Fetal bovine serum (FBS) and Dulbecco's modified Eagle medium (DMEM) purchased from Gibco (USA) and mouse-derived B16F10 (melanoma cell line) purchased from the Korean Cell Line Bank were used for cellular experiments. Cells were cultured in DMEM (Gibco) supplemented with 10% FBS (Gibco) and 1% antibiotic-antimycotic (Gibco) in an incubator at 37° C. and 5% CO$_2$. Cells were passaged every 3-4 days. Cultured B16F10 cells were detached with 0.05% trypsin-EDTA and inoculated into each well of a 24-well plate at the same density (2.0×10$^4$ cells/well). 24 hafter inoculation, cells were treated with α-MSH (100 nM) and each test drug. Cells were cultured for 3 days. After completion of the culture, cells were treated with 1 N NaOH and the reaction was allowed to proceed at 80° C. for 1 h to elute melanin from cells. The amount of melanin was determined by measuring the absorbance at 405 nm. Kojic acid and arbutin were used as positive controls. The results are shown in FIG. 3.

Figure 3:
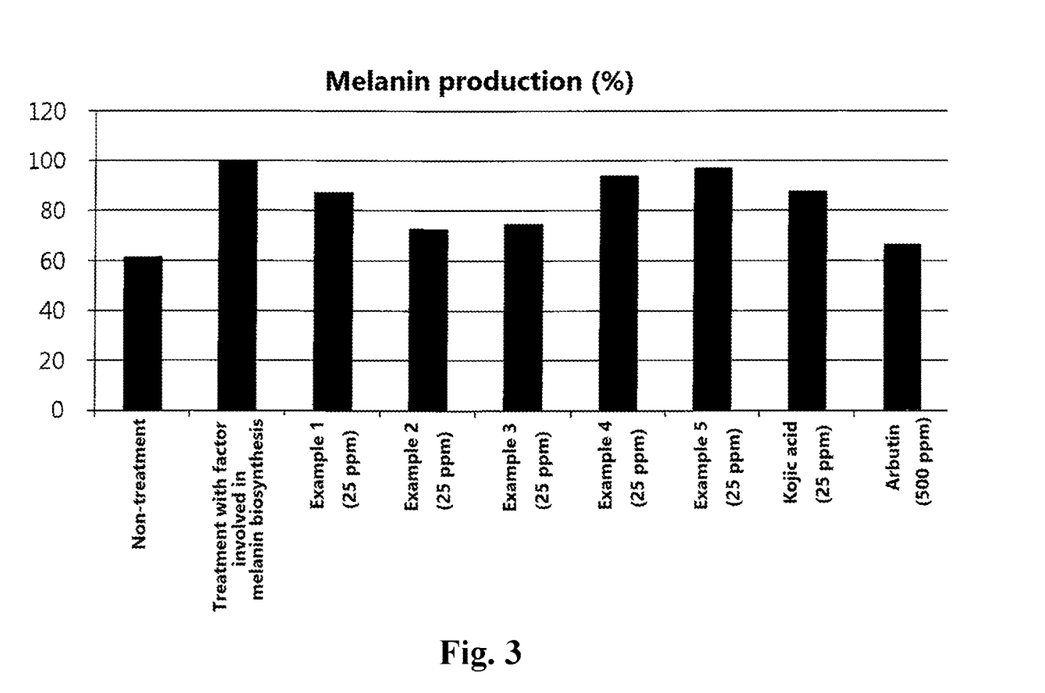
FIG. 3 shows inhibitory effects of compounds prepared in Examples 1-5 on melanogenesis.

As can be seen from FIG. 3, the compounds of Examples 1-5 showed better inhibitory effects on melanogenesis than arbutin. Some of the compounds of Examples 1-5 were confirmed to show higher activities than kojic acid. These results demonstrate that the phenolic acid derivative compounds of the present invention are effective in skin whitening due to their ability to inhibit melanogenesis.

The invention claimed is:
1. A compound represented by Formula 3 or salt thereof:

[Formula 3]

wherein R$_2$ is H or C$_1$-C$_3$ alkyl, each R$_3$ is methyl, and R$_5$ is an amino group or an acetamido group.

2. The compound or salt thereof according to claim 1, wherein the compound or salt thereof is (R)-ethyl-2-amino-3-(4-hydroxy-3,5-dimethoxybenzoylthio)propanoate or (R)-methyl-2-acetoamido-3-(4-hydroxy-3,5-dimethoxybenzoyl-thio)propanoate.

3. A composition for skin whitening comprising the compound or salt thereof according to claim 1 as an active ingredient.

4. An antioxidant cosmetic composition for preventing or treating an oxidation-derived skin abnormality or disease comprising the compound or salt thereof according to claim 1 as an active ingredient.

5. The antioxidant cosmetic composition according to claim 4, wherein the oxidation-derived skin abnormality or disease is selected from skin aging, wrinkling, skin pigmentation, and combinations thereof.

6. A cosmetic composition comprising 0.01 to 10% by weight of the compound or salt thereof according to claim 1.

* * * * *